(12) United States Patent
Lindenthaler

(10) Patent No.: US 6,361,494 B1
(45) Date of Patent: Mar. 26, 2002

(54) ELECTRODE AND METHOD FOR MEASURING MUSCLE ACTIVITY IN THE PHARYNGEAL AIRWAYS

(75) Inventor: Werner Lindenthaler, Oberperfuss (AT)

(73) Assignee: MED-EL. Elektromedizinische Gerate Ges.m.b.H., Innsbruck (AT)

( * ) Notice: Subject to any disclaimer, the term of this patent is extended or adjusted under 35 U.S.C. 154(b) by 0 days.

(21) Appl. No.: 09/313,731

(22) Filed: May 18, 1999

Related U.S. Application Data

(60) Provisional application No. 60/085,824, filed on May 18, 1998.

(51) Int. Cl.$^7$ .................................................. A61N 1/05
(52) U.S. Cl. ........................................................ 600/373
(58) Field of Search ................................ 600/373, 546, 600/534, 529

(56) References Cited

U.S. PATENT DOCUMENTS

| | | | |
|---|---|---|---|
| 5,190,053 A | * 3/1993 | Meer | 128/787 |
| 5,212,476 A | 5/1993 | Maloney | 340/825.19 |
| 5,373,852 A | 12/1994 | Harrison et al. | 128/733 |
| 5,546,952 A | * 8/1996 | Erickson | 128/716 |

OTHER PUBLICATIONS

Lynn et al., "Influences of Electrode Geometry on Bipolar Recordings of the Surface Electromyogram," *Med. Biol. Eng. Comput.* 16(6): 651–660 Nov. 1978.

Doble et al., "A Noninvasive Intraoral Electromyographic Electrode for Genioglossus Muscle," *J. Applied Physiology* 58(4): 1378–1382 Apr. 1985.

Lufkin et al., "Tongue and Oropharynx: Findings on MR Imaging," *Radiology* 161(1): 69–75, Oct. 1986.

Kassel et al., "MRI of the Floor of the Mouth, Tongue and Orohypopharynx," *Radiol. Clin. North. Am.* 27(2): 331–351, Mar. 1989.

Takada et al., "Tongue, Jaw, and Lip Muscle Activity and Jaw Movement During Experimental Chewing Efforts in Man," *J. Dent. Res.* 75: 1598–1606, Aug. 1996.

* cited by examiner

*Primary Examiner*—William E. Kamm
(74) *Attorney, Agent, or Firm*—Bromberg & Sunstein LLP

(57) ABSTRACT

An electrode for placement in a human mouth for the measurement of muscle activity in the pharyngeal airway. The electrode includes at least one leg extending from a planer face so as to make electrical contact with the genioglossus muscle. The electrode permits a reduction in the number of patients requiring overnight polysomnography to prediagnose people with sleep apnea.

18 Claims, 6 Drawing Sheets

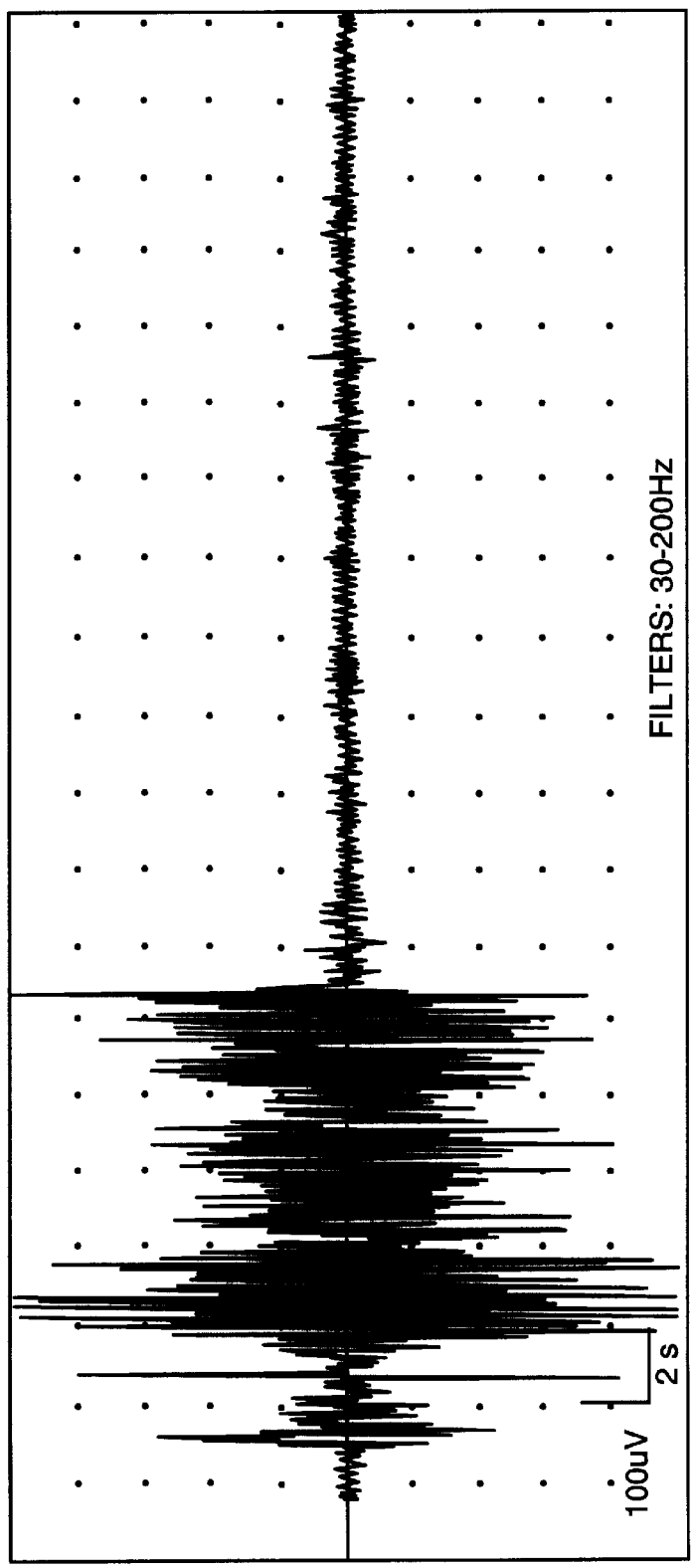

ELECTRODE AND METHOD FOR MEASURING MUSCLE ACTIVITY IN THE PHARYNGEAL AIRWAYS

This application claims the benefit of U.S. Provisional Application No. 60/085,824, filed May 18, 1998, which is hereby incorporated herein by reference.

TECHNICAL FIELD

The present invention relates to an electrode and method for measuring muscle activity in the pharyngeal airways and, in particular, to diagnosing sleep apnea in wakeful patients.

BACKGROUND TO THE INVENTION

An estimated 2% to 4% of the population are believed to suffer from sleep apnea syndrome. Sleep apnea is a condition that results from a reduction in air intake through the air passage of sleeping individuals. This problem arises as a result of weak muscle tone in the throat and although compensated for during waking hours, gives rise to symptoms of fatigue during the day, poor quality sleep at night, and heavy snoring during sleep. Diagnosis of sleep apnea has been carried out in sleep laboratories where the patient is monitored at night during sleep in a process called nocturnal polysomnography. This diagnostic test is expensive, time consuming, and must be administered by highly trained technicians. Consequently, availability of the test is limited.

The monitoring of sleep apnea traditionally took the form of electromyographic (EMG) analyses of the genioglossus muscle. The analysis relied on intramuscular electrode recordings which were made by inserting a needle or wire electrode into the body of the muscle just below the teeth. With the needle electrodes it is not possible to make quantative comparisons to the EMG recordings if the electrode is moved or replaced because the tip of the needle cannot be placed at exactly the same position within the muscle. Consequently, the needle electrodes measure activities from different anatomical and architectural organizations and different fiber types.

An alternative approach was suggested by Doble et al. in J. Applied Physiology 58 (4): 1378–82 (1985). This approach employed an intra-oral surface recording electrode for monitoring the genioglossus EMG activity. A mouth electrode was fitted to the teeth in order to make quantitative measurements of EMG activity. Doble's mouthpiece electrode was bulky and interfered with the action of the tongue. Under Doble's approach, patients were seated in a dental chair with their neck flexed forward at an angle of 30 degrees and were required to maintain this head position during the tests.

Takada et al., J. Dent. Res. 75: 1598–1606 (1996), conducted further studies to examine tongue, jaw and lip muscle activity utilizing an electrode assembly that relied on fixation to the teeth.

SUMMARY OF THE INVENTION

The present invention provides an electrode, apparatus and method for measuring muscle activity in the pharyngeal airways and sleep apnea while the subject is awake. The invention is convenient and increases availability of testing to patients. The invention also reduces the cost of diagnosis.

In a preferred embodiment of the invention, an electrode is provided for measuring muscle activity in the pharyngeal airways, comprising: an electrode body for placement in a human mouth, the body having a face defining a plane, and at least one leg extending from the face, the leg having an electrical contact such that when the electrode body is placed in the mouth, the contact is in communication with the genioglossus muscle.

The body is preferably formed from a biologically inert material. In a further embodiment, the at least one leg is between 2 mm and 8 mm in length. In another preferred embodiment, the at least one leg extends from the face at a substantially 90 degrees. The body also preferably has four legs, the four legs each extending from the face at substantially 90 degrees angles such that the legs form the vertices of a square.

In a preferred embodiment, the body of the electrode has at least two legs and is bifurcated such that each part of the body has one leg which can be placed on each side of a frenum in a human mouth. In yet another embodiment, the electrode body is formed into a crescent contour.

In another preferred embodiment, a method is provided for measuring muscle activity in the pharyngeal airways comprising: placing an electrode having an electrode body in a mouth, the body having at least one electrical contact such that when the electrode body is placed in the mouth, the contact is in communication with the genioglossus muscle; recording signals received from the electrode; and comparing the signals to signals obtained from normal pharyngeal muscle activity. To diagnose sleep apnea, the signals are compared to signals obtained from people without sleep apnea.

In a further embodiment, a method is provided for diagnosing sleep apnea wherein the signals are compared to signals taken from the same patient at a different session and further comprising: amplifying the signals; filtering the signals; integrating the signals; and feeding the results into a computer for analysis.

In another preferred embodiment, an apparatus for diagnosing sleep apnea is provided comprising: an electrode having an electrode body for placement in a patient's mouth, the body having at least one electrical contact such that, when the electrode body is placed in the mouth, the contact is in communication with the genioglossus muscle; an amplifier in electrical communication with the electrode to receive EMG signals from the electrode; a signal filter in electrical communication with the amplifier; a rectifier in electrical communication with the filter such that the rectifier receives the filtered signal; and a signal integrater in electrical communication with the rectifier whereby the rectified signal is integrated on a moving time average basis.

BRIEF DESCRIPTION OF THE FIGURES

These and other features and advantages of the present invention will become better understood with reference to the following description and accompanying drawings wherein:

FIG. 2(*b*) shows a side view of the electrode where the legs extend 4 mm below the plane of the electrode body.

FIGS. 4(*a*)–(*c*) show typical EMG readings obtained from the electrode of the invention wherein:

FIG. 4(b) shows an EMG recording of swallowing, protrusion of the tongue against the upper front teeth, and quiet breathing.

DETAILED DESCRIPTION OF SPECIFIC EMBODIMENTS

In an individual with reduced pharyngeal airway size, increased intraluminal pressure is generated during inspiration. The increased pressure stimulates upper airway muscle activity, thus dilating the pharyngeal airway and maintaining airway patency while awake. This difference in patency results in measurable differences in waking airway luminal size in apnea patients. Furthermore, apnea patients appear to have greater pharyngeal dilator muscle activity during wakefulness than is encountered in normal healthy subjects. Measurement of these differences in muscle activity is the principle that underlies the present invention.

The location of the geniohyoideus, mylohyoideus, mylohyoideus and digastricus muscles relative to the genioglossus muscles can be verified by MRI and EMG signals from these muscles can be separated from EMG signals from the genioglossus muscle. EMG signals produced by the longitudinal and transverse fibers of the muscles in the body of the tongue can also be isolated.

Using the electrode and method of the invention, a diagnostic result may be obtained during wakefulness within a few minutes. The test is non-invasive and painless to the patient. Administration of the test does not require the assistance of a technician or physician with specialized knowledge or diagnostic expertise.

Figure 1:
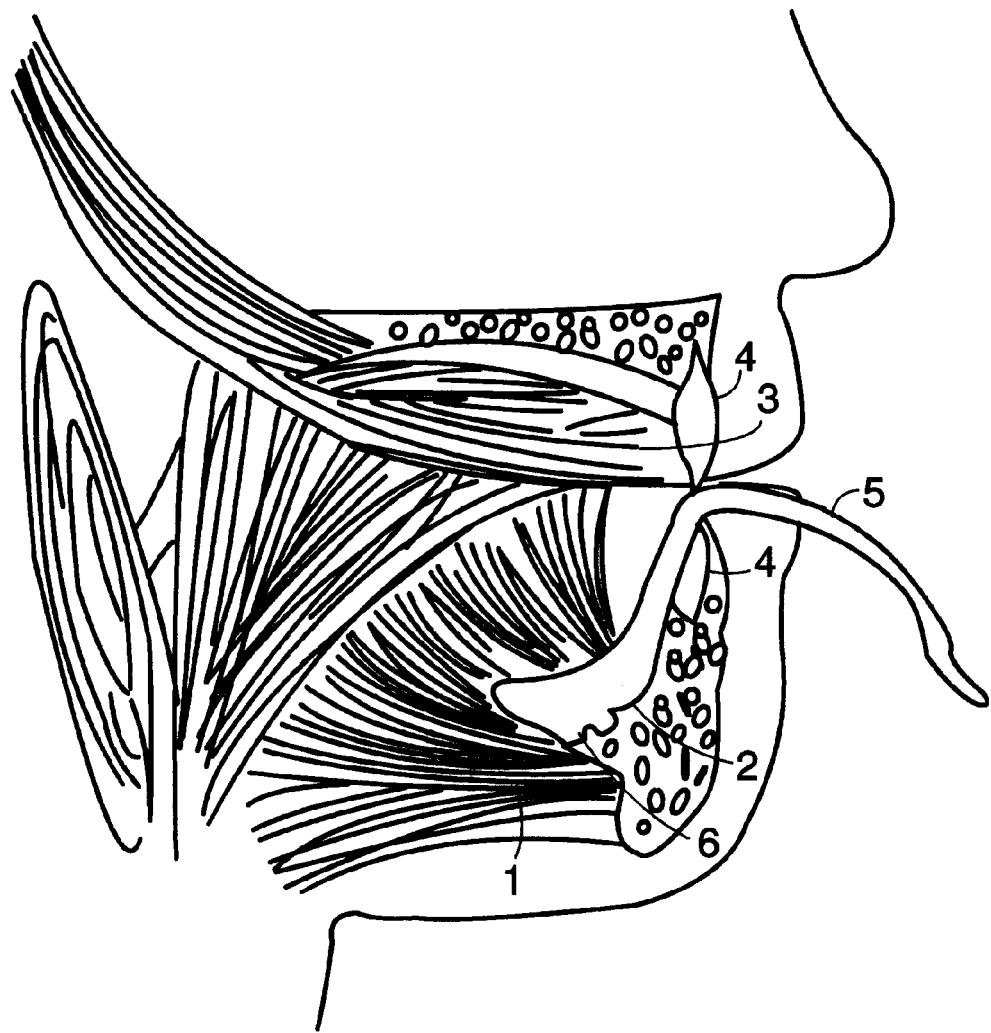
FIG. 1 shows cross section of the mouth in the vertical plane showing the electrode body in position on the mouth floor behind the teeth.

FIG. 1 shows the positioning of an intra-oral bipolar surface electrode 2 for measuring the EMG of the genioglossus muscle 1. The electrode body sits in the floor of the mouth under the tongue 3 and behind the teeth 4 with an electrode line 5 emerging through the lips of the mouth. The electrode is positioned between the tongue 3 and the lower jaw, so that it is kept in firm hold by these structures without further fixation to the teeth 4 or the neighboring tissue by glue, screws, needles, or anything else. The legs 6 lie lateral to the frenum and make a bipolar recording of the surface genioglossus muscles. In a preferred embodiment, the legs lie about 3 mm lateral to the frenum. Electrical contacts 7 bared at an end portion of the legs 6 lie in close contact with the superior surface of the genioglossus muscle 1.

Figure 2A:
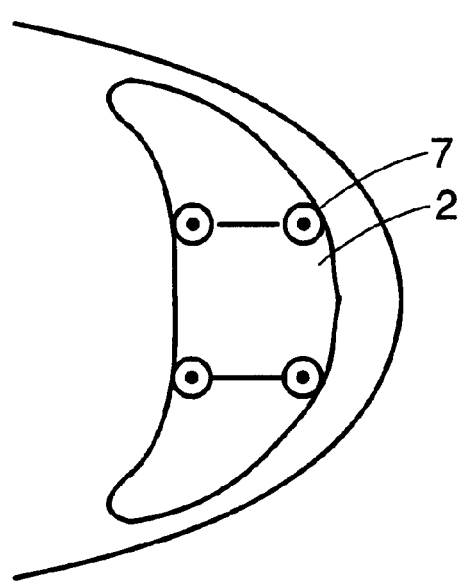
FIG. 2(*a*) shows a top plan view of the electrode where the legs are arranged at the vertices of a square.
Figure 2B:
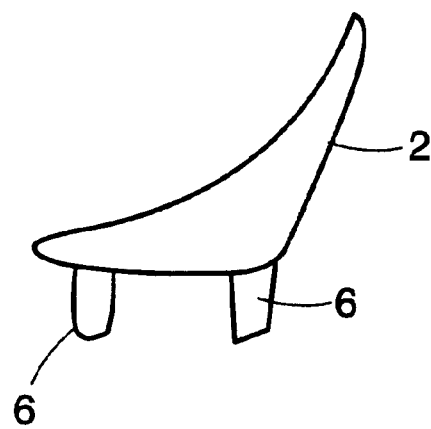

FIGS. 2(a) and 2(b) show the electrode in a crescent contour wherein each arm contains a pair of legs 6. In a preferred embodiment, the crescent shaped electrode body measures 26 mm in a vertical plane and 15 mm in a horizontal plane. The two pairs of contacts 7 may be parallel as shown in FIG. 2(a) although alternative configurations may be used. According to FIG. 2(a), the two leg pairs are positioned 7.5 mm apart so as to form a square. Leg pairs may be positioned as little as 2 mm apart and as much as 11 mm apart.

FIG. 2(b) shows the legs 6 extending down from the electrode body 2 onto the mouth floor, where, in a preferred embodiment, the terminals 6 are between 2 mm and 8 mm in length.

Figure 3:
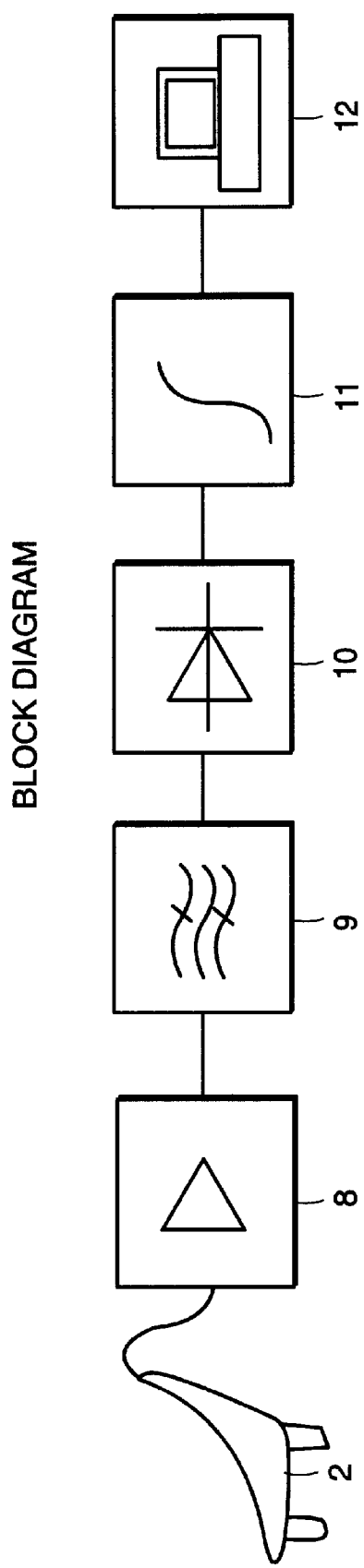
FIG. 3 shows a schematic of the processing of the signal received by the electrode in the mouth.

FIG. 3 shows how the signal received from the electrode 2 is processed. The signal travels to an amplifier 8, to a filter 9, a rectifier 10, an integrator 11, and, finally, to a computer 12. The signal is recorded using recording methods known in the art and is compared to signals obtained from normal healthy patients or from signals taken from the same patient at different sessions.

Figure 4A:
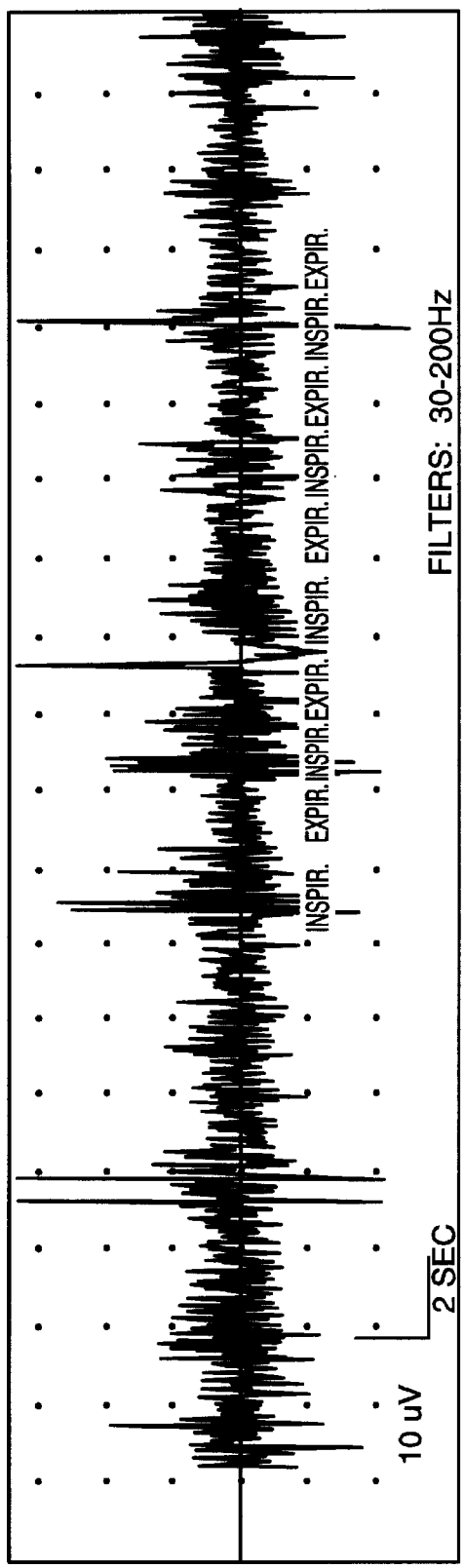
FIG. 4(a) shows an EMG recording of quiet breathing.
Figure 4C:
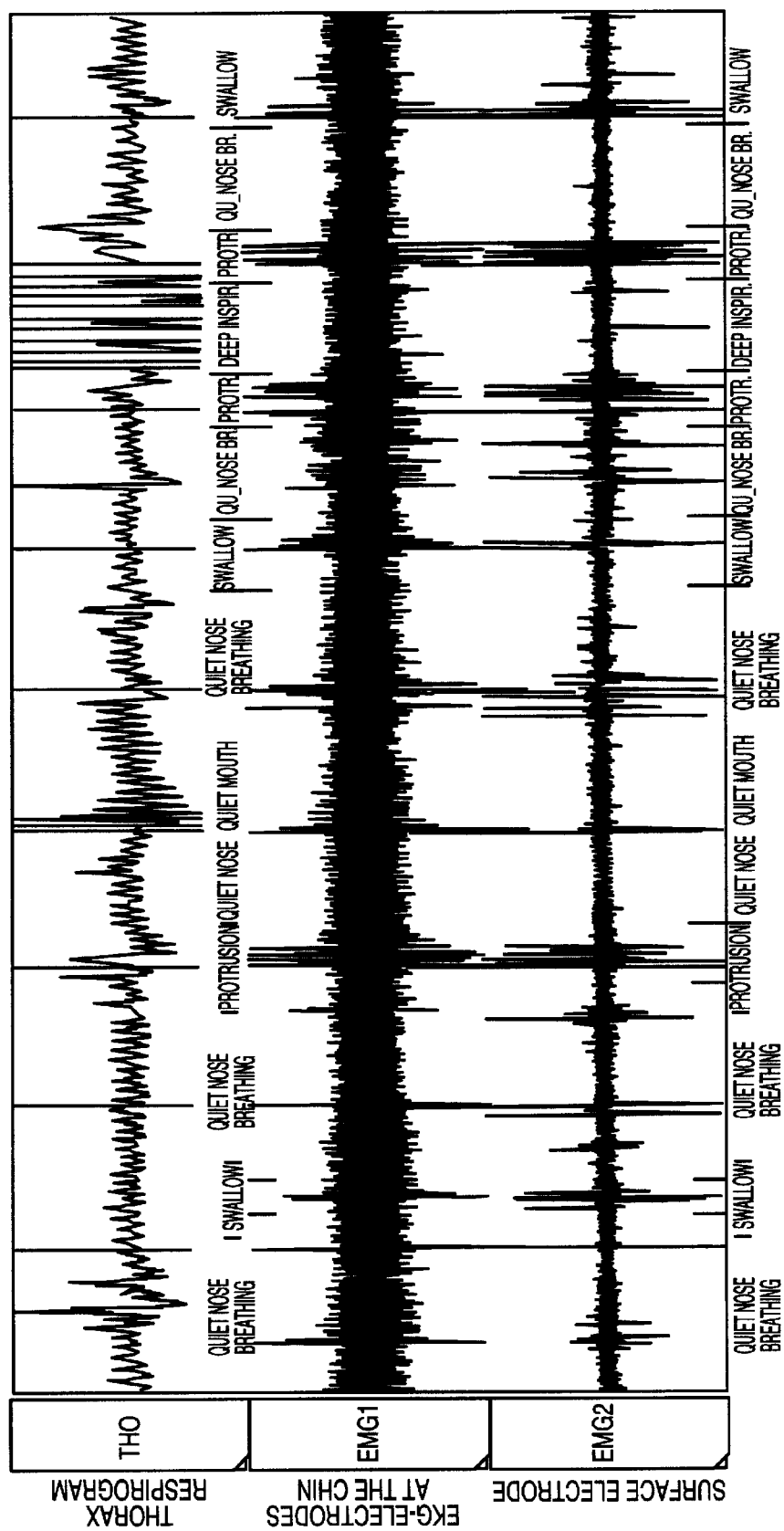
FIG. 4(c) shows an EMG recording of quiet breathing through the nose, through the mouth, deep inspirations, swallowing and tongue protection.

FIGS. 4(a)–(c) show EMG recordings obtained by the electrode of the invention. The electrical activity of the genioglossus muscle was measured by the method of the invention. The EMG signal was amplified, filtered between 50 Hz and 200 Hz, rectified, and integrated on a moving time average basis with a time constant of 100 ms.

Maximum EMG amplitude was measured for forceful protrusion of the tongue against the maxillary alveolar ridge. If the amplitude was higher then the individual's maximum, swallowing was taken to define 100%. To define 0%, the EMG was also measured during quiet nasal breathing while the patient was lying down supinely. An ECG electrode was glued to the forehead as a reference. The EMG was then scaled between 0 and 100%.

If the EMG of the genioglossus muscle was lower than 7.5% of the individual's own maximum, the person being measured was prediagnosed to have no Sleep Apnea Syndrome. If the genioglossus EMG was computed to be higher than 7.5% of the maximum, then the person was prediagnosed to be a Sleep Apnea patient.

Measurements obtained over a two minute period will be sufficient to make a diagnosis, however different time periods may be selected. It is not a requirement of the test to cause the patient's neck to be flexed during the diagnostic test. Respirophasic activation of the genioglossus pulls the base of the tongue forward during inspiration and helps prevent negative pressures from drawing the tongue into the pharynx and occluding the airway.

The electrode may be formed from any biologically inert material that is electrically isolating and preferably sterilizable or disposable. Dental acrylic, athletic mouth guard material, and dental impression material would be suitable. Further, the electrode need not be fitted to each patient because it can be fabricated in different sizes and one with optimal fit to the lower jaw can be chosen.

The electrode can be formed and positioned without fixation to the teeth so that it is free to move with the floor of the mouth and always stayed in firm contact with the superior surface of the genioglossus muscle. The electrode is able to record the muscle activity of a given action in a stable and reproducible manner even though the floor of the mouth may move up and down and the electrode may be exposed to saliva.

The shape and positioning of the electrode, and the configuration of the legs, enables bipolar recordings to be made of the two bodies of the genioglossus muscle either separately or together. The lateral spacing of the leg pairs is decisive for the closest contact and maximizes the resulting EMG signal. Additionally, the close contact to the genioglossus muscle has the advantage of minimal interference from other muscles because most of the energy in the EMG is derived from fibers lying within the radius of the electrode legs. Consequently, by using the electrode of the invention, the low pass, filtered, overall action potentials of the muscle fibers is registered in a specific area around the contacts which is defined and remains the same at different sessions because of the relative exact fit between the lower jaw and the tongue.

What I claim is:

1. An electrode for measuring muscle activity in the pharyngeal airways comprising:

an electrode body for placement in a human mouth, the body having a face defining a plane, and at least one leg extending from the face, the leg having an electrical contact such that, when the electrode body is placed in the mouth, the contact is in communication with the genioglossus muscle without fixation of the body to teeth.

2. An electrode according to claim 1, wherein the body is formed from a biologically inert material.

3. An electrode according to claim 1, wherein the at least one leg is between 2 mm and 8 mm in length.

4. An electrode according to claim 1, wherein the at least one leg extends from the face at a substantially 90 degree angle.

5. An electrode according to claim 1, wherein the body has four legs, the four legs each extending from the face at substantially 90 degree angles such that the legs form the vertices of a square.

6. An electrode according to claim 1, wherein the body has at least two legs and is bifurcated such that each part of the body has one leg which can be placed on each side of a frenum in a human mouth.

7. An electrode according to claim 6, wherein the at least two legs each extend from the face at substantially 90 degree angles.

8. An electrode according to claim 7, wherein the body is formed into a crescent contour.

9. An electrode according to claim 8, wherein the body measures between 15 mm and 35 mm in a vertical plane and between 5 and 25 mm in a horizontal plane.

10. A method for diagnosing sleep apnea comprising:

placing an electrode having an electrode body in a patient's mouth, the body having a face defining a plane, and at least one leg extending from the face, the leg having an electrical contact such that, when the electrode body is placed in the mouth, the contact is in communication with the genioglossus muscle;

recording signals received from the electrode; and comparing the signals to signals obtained from people without sleep apnea.

11. A method according to claim 10, wherein the signals are compared to signals taken from the same patient at a different session and further comprising:

amplifying the signals;

filtering the signals;

integrating the signals; and feeding the results into a computer for analysis.

12. A method according to claim 11, wherein the signals are filtered between 50 Hz and 200 Hz.

13. A method according to claim 12 wherein, the signals are integrated on a moving time average basis with a time constant of 100 ms.

14. An apparatus for diagnosing sleep apnea comprising:

an electrode having an electrode body for placement in a patient's mouth, the body having a face defining a plane, and at least one leg extending from the face, the leg having an electrical contact such that, when the electrode body is placed in the mouth, the contact is in communication with the genioglossus muscle without fixation of the body to teeth;

an amplifier in electrical communication with the electrode to receive EMG signals from the electrode;

a signal filter in electrical communication with the amplifier;

a rectifier in electrical communication with the filter such that the rectifier receives the filtered signal; and a signal integrator in electrical communication with the rectifier whereby the rectified signal is integrated on a moving time average basis.

15. An apparatus according to claim 14, wherein the amplified signal is filtered between 50 Hz and 200 Hz.

16. An apparatus according to claim 14, wherein the rectified signal is integrated on a moving time average basis with a time constant of 100 ms.

17. An electrode according to claim 1, wherein the at least one leg is substantially cylindrical and includes a radius such that a substantial portion of electromagnetic energy measured by the electrode is derived from an area of the mouth within the radius.

18. An electrode according to claim 14, wherein the at least one leg is substantially cylindrical and includes a radius such that a substantial portion of electromagnetic energy measured by the electrode is derived from an area within the radius.

* * * * *